United States Patent [19]

Yang et al.

[11] Patent Number: 4,859,597

[45] Date of Patent: Aug. 22, 1989

[54] PRODUCTION OF PHAGE AND PHAGE-ASSOCIATED LYSIN

[75] Inventors: Huei-Hsiung Yang, Rockville; Stephen F. Hiu; John L. Harris, both of Columbia, all of Md.

[73] Assignee: Igene Biotechnology, Inc., Columbia, Md.

[21] Appl. No.: 77,874

[22] Filed: Jul. 27, 1987

[51] Int. Cl.$^4$ .............................................. C12N 7/02
[52] U.S. Cl. ................................. 435/239; 435/68; 435/91; 435/235; 435/259; 435/183; 435/885; 424/89
[58] Field of Search ............... 435/235, 239, 259, 885; 424/89

[56] References Cited

PUBLICATIONS

Sozzi et al–Chem. Abst., vol. 92, (1980), p. 124, 770v.
Moynet et al–Chem. Abst., vol. 102, (1985), p. 182, 091k.
Mullan et al. Chem. Abst., vol. 102, (1985), p. 41995w.
Mullan et al. Chem. Abst., vol. 102, (1985), p. 59037v.

*Primary Examiner*—Sam Rosen
*Attorney, Agent, or Firm*—Millen, White & Zelano

[57] ABSTRACT

A method for producing a lysin-free phage inoculum, which comprises:
(a) inoculating a growing Streptococcal culture with phage,
(b) incubating the culture for a plurality of lytic cycles of phage until the cells are completely lysed to obtain a lysate, and
(c) removing cell debris and free lysin from the lysate to form a lysin-free phage suitable for use as an inoculum.

A method for producing lysin is also disclosed.

16 Claims, No Drawings

PRODUCTION OF PHAGE AND PHAGE-ASSOCIATED LYSIN

DESCRIPTION OF THE INVENTION

1. Technical Field of the Invention

This invention relates to a process for the production of high titers of phage-associated lysin by growing Streptococcus sp. cells to high density and infecting the Streptococcal culture with an appropriate amount of phage suspension containing no free lysin. In the process, the phages are separated from cell debris and active lysin and are concentrated. The concentrated phage solution is used to infect growing Streptococcal cells at high cell density. After inoculation with phage, the infected Streptococci are harvested at a precise time and resuspended in buffer to release maximal amounts of phage-associated lysin.

2. Background Art

Lysates of Group C Streptococci which are infected with C1 bacteriophage contain an enzyme, Lysin, that has the ability to lyse Groups A, C, and E Streptococci and their isolated cell walls. Maxted, W. R. (1957) J. Gen. Microbiol. 16: 584. This enzyme was found to be ideal for the isolation of Group A Streptococcal cell wall components, M protein and C carbohydrate.

A new application of this enzyme for the detection of Streptococcal throat infections was disclosed by Vincent A. Fischetti and David Bernstein. To make this new application commercially attractive, it is essential to produce the phage-associated lysin efficiently.

In the research laboratory, a procedure for making small quantities of lysin has been documented. However, the process described has certain inherent disadvantages from the commercial standpoint, in that a large volume of phage lysate is required as inoculum for the preparation of phage, and that long periods of time (4 weeks) are required to inactivate a free lysin present in the supernatant. In addition, the titers obtained are considerably low and inconsistent.

A lysin-free phage inoculum is essential for the preparation of both lysin and phage inoculum. Besides inactivation by aging, physical separation provides a nondestructive means to remove undesirable components from the phage inoculum. Among methods of physical separation, ultrafiltration is a commercially available system which will separate components according to molecular size.

Molecules of lysin are smaller than phage particles. By selecting the proper membrane, the phage can be retained and concentrated while lysin passes through. Concentrated phage is then washed with buffer to remove free lysin, and the phage concentrate is ready to be used or stored for future use.

According to the prior art, the aged phage solution containing inactivated lysin is used to inoculate a Streptococcal culture grown to 0.16 OD at 650 nm. The mixture is allowed to remain at 37° C. for 20 minutes at which time the infected cells are harvested and resuspended in buffer. The cells are allowed to lyse, releasing phage and the lytic enzyme.

In general, the total yield of intracellular enzyme is a function of cell mass. The titer of lysin should increase with increasing concentrations of infected Streptococci. In the prior art, the phage concentration was constant so that any increase in the Streptococcal cell density could not increase the number of infected Streptococci or the enzyme titer. According to the present invention, the phase can be concentrated. Thus, the Streptococci can be grown to higher density and can be infected by concentrated phage. As a result, the titer of lysin can be increased.

DISCLOSURE OF THE INVENTION

Accordingly, it is a general object of the present invention to provide an improved process of preparing phage suspension containing no free lysin and of producing higher titers of lysin which can be used in diagnostic tests for the identification of Group A Streptococci from infected tissue.

The advantage of the new method for phase production are three-fold. The amount of phage required to generate a new batch of phage inoculum is greatly reduced. The number of phage produced per initial phage is improved $10^4$ fold. In addition, the phage lysate used as inoculum for phage production may contain active lysin since lysis "from without" does not occur because of the high dilution factor.

The phage lysate of the present invention is substantially free of lysin, i.e. a 1 : 4 dilution with Streptococcus cells will not lyse the cells when incubated at 37° C. for 15 minutes. Because the lysin content is kept low, there will be no extracellularly induced lysis prior to the first phage replication cycle. Since the phage replication cycle releases about 100 phage particles every 20 minutes in comparison with the Streptococcus replication of two cells every 20–30 minutes, this "multicyclic" process can readily produce phage concentrations of $10^{10}$–$10^{11}$ PFU/ml.

Initial cell infection with phage is preferably made from $10^9$ PFU/ml stock added to a streptococcal culture of O.D. of about 0.2 at 650 nm, representing an initial inoculum of about $10^4$ PFU/ml. While some lysin builds up in the course of the multicyclic culture process and not every phage particle will infect a new cell, there is a maximum concentration of phage at which all cells will be lysed. Nonetheless, this process can generate $10^{10}$ phage particles/ml from an inoculum of only $10^4$/ml in only four hours.

Upon study of the specification and appended claims, further objects, feature and advantages of the present invention will become more fully apparent to those skilled in the art to which this invention pertains.

BEST MODE FOR CARRYING OUT THE INVENTION

Briefly, the above and other objects, features, and advantages of the present invention are attained in one aspect thereof by providing a method for producing a lysin-free phage inoculum, which comprises:

(a) inoculating a growing Streptococcal culture with phage,
(b) incubating the culture for a plurality of lytic cycles of phage until the cells are completely lysed to obtain a lysate, and
(c) removing cell debris and free lysin from the lysate to form a lysin-free phage suitable for use as an inoculum.

DETAILED DESCRIPTION OF THE INVENTION

In one aspect, the present invention provides an improved process of preparing phage suspension containing no free lysin and of producing higher titers of lysin which can be used in diagnostic tests for the identification of Group A Streptococci from infected tissue.

The advantages of the new method for phage production are three-fold. The amount of phage required to generate a new batch of phage inoculum is greatly reduced. The number of phase produced per initial phage is improved $10^4$ fold. In addition, the phage lysate used in inoculum for phage production may contain active lysin since lysis "from without" does not occur because of the high dilution factor.

A phage inoculum, which contained no free lysin, was prepared by growing the Streptococcal cells in Todd-Hewitt broth at 37° C. to a cell density of 0.10 to 1.0 OD, (preferably 0.1 to 0.4 OD) at 650 nm before the proper amount of phage solution was added. After phage infection, the culture was incubated to allow for several lytic cycles of phage to occur before the cells were completely lysed. Cell debris were removed by filtration through a 0.2 - membrane. This phage preparation containing active free lysin was passed through a second ultrafiltration system with a membrane which had a molecular weight cutoff between 100,000 and 300,000. The phage was separated from free lysin and concentrated. The final concentrated phage was washed and then used as an inoculum for lysin production or for preparation of the next batch of phage.

For the production of lysin, the above described procedure was followed with some modification. The phage-infected Streptococcal cells were harvested 15–20 minutes after concentrated phage was inoculated into a Streptococcal culture grown to a cell density greater than 0.1 at 650 nm. The harvested cells were resuspended in 0.05 M phosphate buffer, pH 6.1, containing $5 \times 10^{-4}$ M dithiothreitol (DTT) and 5 mg bovine pancreatic deoxyribonuclease. The suspension was then incubated at 37° C. for 30–60 minutes during which time the cells lysed, releasing the lytic enzyme (lysin). Ethylene diamine tetraacetic acid (EDTA) was added to a final concentration of 0.005 M. The cell debris and phage was removed by ultracentrifugation at 30,000 rpm for 4 hours at 4° C. in a Sorvall A641 rotor (Ivan Sorvall, Inc., Norwich, Conn.). The lysin solution was collected and could be used as a diagnostic reagent for detecting Streptococcal infection.

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, the temperatures are set forth uncorrected in degrees Celsius; unless otherwise indicated, all parts and percentages are by weight.

EXAMPLE 1

A phase inoculum was prepared by the new multicyclic process. A 6.5-liter culture of Streptococcal cells was grown to an optical density of 0.20 at 650 nm in Todd-Hewitt broth, inoculated with phage (30 ml, $1.0 \times 10^7$ pfu/ml), and incubated until lysis occurred (90 minutes). The initial phage titer immediately after inoculation was $4.6 \times 10^4$ pfu/ml. After complete cell lysis (90 minutes) the phage titer was $4.5 \times 10^9$ pfu/ml, a $10^5$ increase.

As a control, a phage inoculum was prepared according to published procedure. A 12-liter culture of Streptococcal cells was grown to an optical density of 0.15 at 650 nm in Todd-Hewitt broth, inoculated with phage (3 liters, $2.8 \times 10^9$ pfu/ml) and incubated until lysis occurred (45 minutes). The initial phage titer immediately after inoculation was $5.6 \times 10^8$ pfu/ml. After complete cell lysis (45 minutes), the phage titer was $8.6 \times 10^9$ pfu/ml, a 15-fold increase over the starting titer.

EXAMPLE 2

Phage inoculum can be concentrated and free lysin removed by the new process. In prior art, this phage preparation was stored at 4° C. for 4 weeks to allow the residual lysin to become inactive, thus preventing lysis by the enzyme when phage lysate was added to the Group C cells for enzyme preparation (Fishchetti, V. A., Gotschlich, E. C. and Bernheimer, A. W. (1971) J. Exp. Med. 133: 1105–1117).

Accordingly to the present invention, the lysate can be processed immediately after lysis has occurred. The lysate was passed through a Millipore GVLP 0.2 u membrane cassette to remove uninfected cells and cell debris. The filtrate then went through a Millipore PTMK 300K membrane cassette which concentrated the phage an removed the free lysin. The resulting phage retentate was washed with a buffer containing 2 g/l sodium chloride, 0.4 g/l dibasic sodium phosphate and 2.5 g/l sodium carbonate, pH 7.5. This washed phage retentate, containing no active free lysin, was ready to be used as an inoculum for lysin production. The results of phage concentration and lysin removal through the 300K membrane was shown in Tables 1 and 2, respectively.

TABLE 1

|  | Phage Titer (pfu/ml) | Volume (ml) | Total Phage (pfu) |
| --- | --- | --- | --- |
| Starting material | $1.2 \times 10^9$ | 15,000 | $1.8 \times 10^{13}$ |
| Concentrate | $1.8 \times 10^{10}$ | 940 | $1.7 \times 10^{13}$ |
| Washed concentrate | $2.0 \times 10^{10}$ | 800 | $1.6 \times 10^{13}$ |
| Filtrate | $9.5 \times 10^7$ | 14,380 | $1.4 \times 10^{12}$ |

TABLE 2

|  | Lysin titer (units/ml) | Volume (ml) | Total Lysin (units) |
| --- | --- | --- | --- |
| Starting material | 16 | 15,000 | 240,000 |
| Concentrate | 22 | 940 | 20,680 |
| Washed concentrate | 1.9 | 800 | 1,520 |
| Filtrate | 19 | 14,380 | 273,220 |

EXAMPLE 3

The improved process of producing lysin is described as follows. Group C Streptococcal strain 26RP66 (ATCC #21597) was grown in 12-liters of Todd-Hewitt broth at 37° C. to an O.D. of 0.41 at 650 n. Three liters of Group C bacteriophage (C1) (ATCC #21597-B1) containing $2.4 \times 10^{10}$ pfu/ml was added to the Streptococcal culture. The mixture was allowed to remain at 37° C. for 16 minutes at which time the infected culture was poured over ice cubes to reduce the temperature of the broth to below 15° C. The infected cells were then harvested in a refrigerated centrifuge at $3700 \times$ g and resuspended in 0.05 M phosphate buffer, pH 6.1 containing $5 \times 10^{-3}$ M dithiothreitol and 5 mg of bovine pancreatic deoxyribonuclease I (Boehringer, Grade II). The cells lysed, releasing the lytic enzyme. Cell debris and phage were removed by centrifugation at 30,000 rpm for 4 hours in a Sorvall A641 rotor. The enzyme solution was aliquoted, tested for its ability to lyse Group A streptococci, and stored at 70° C.

EXAMPLE 4

The number of units per ml in a batch of enzyme is determined to be the reciprocal of the highest dilution of enzyme required to reduce the $OD_{650}$ of a suspension of Group A Streptococci from 0.3 to 0.15 in 15 minutes at 37° C. The yield of lysin in a 12 liter batch obtained by infecting different cell densities of Streptococci with increasing phage inoculum is shown in Table 3.

TABLE 3

| Cell Density ($OD_{650}$) | Phage Inoculum (pfu) | Lysin Titer (unit/batch) |
| --- | --- | --- |
| prior art: | | |
| 0.10 | | $4.0-7.1 \times 10^4$ |
| 0.21 | $2.9 \times 10^{13}$ | $4.0 \times 10^5$ |
| 0.40 | $2.6 \times 10^{13}$ | $7.0 \times 10^5$ |
| 0.60 | $4.3 \times 10^{13}$ | $9.8 \times 10^5$ |

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

What is claimed is:

1. A method for producing a lysin-free phage inoculum, which comprises:
    (a) inoculating a growing Streptococcal culture with phage,
    (b) incubating the culture for a plurality of lytic cycles of phage until the cells are completely lysed to obtain a lysate, and
    (c) removing cell debris and free lysin from the lysate to form a lysin-free phage suitable for use as an inoculum.

2. A method according to claim 1, wherein the free lysin is removed by ultrafiltration of the lysate through a membrane having a molecular weight cutoff of about 100,000–300,000.

3. A method according to claim 1 wherein the cells are Group C Streptococcus cells.

4. A method of producing lysin, which comprises:
    producing a lysin-free phage inoculum according to the method of claim 1; and then
    inoculating growing Streptococcal cells with the thus-produced Streptococcal lysin-free phage inoculum;
    culturing the cells under conditions suitable for the production of lysin;
    lysing the cells to release the lysin; and
    recovering the lysin from the lysate.

5. A method according to claim 4 wherein the phage is C1.

6. The method of claim 4 wherein the cells are group C Streptococcus.

7. A method of claim 4 wherein the lysate contains at least 70,000 units of lysin per liter of fermentation broth.

8. A method according to claim 4, wherein the cells are Group C Streptococcus cells and wherein the phage is C1.

9. A method according to claim 1, which comprises the further step of (d) concentrating the lysin-free phage-containing lysate obtained in Step (c).

10. A method according to claim 9, wherein the phage is concentrated in Step d) by passing the incubate successively through membranes which first retain and thus separate uninfected cells and cell debris from the phage and next retain the phage and thus separate the lysin from the phage, which is then washed to produce a lysin-free phage concentrate which is also free of cell debris.

11. A method according to claim 9, wherein the starting Streptococcal culture has a cell density of 0.1 to 1.0 OD at 650 nm.

12. A method according to claim 9, wherein the starting Streptococcal culture has a cell density of 0.1 to 0.4 OD at 650 nm.

13. A method according to claim 9, wherein Steps (a), (b), (c) and (d) are repeated, employing as the phage in repeated Step (a) the initially produced phage concentrate obtained in Step (d).

14. A method according to claim 13, wherein the cells are Group C Streptococcus cells; wherein the phage is C1; and wherein Step (c) the free lysin is removed by ultrafiltration of the lysate through a membrane having a molecular weight cutoff of about 100,000–300,000.

15. A method according to claim 8, wherein the step of recovering comprises ultracentrifugation of the lysin-containing lysate to separate the phase and the cell debris therefrom.

16. A method according to claim 15, wherein the starting Streptococcal culture has a cell density of 0.1 to 0.4 OD at 650 n.

* * * * *

UNITED STATES PATENT AND TRADEMARK OFFICE
CERTIFICATE OF CORRECTION

PATENT NO. : 4,859,597

DATED : August 22, 1989

INVENTOR(S) : YANG ET AL

It is certified that error appears in the above-identified patent and that said Letters Patent is hereby corrected as shown below:

Column 6, claim 15, line 47:

reads "containing lysate to separate the phase and the cell"

should read --containing lysate to separate the phage and the cell --

Signed and Sealed this

Nineteenth Day of June, 1990

*Attest:*

HARRY F. MANBECK, JR.

*Attesting Officer*     *Commissioner of Patents and Trademarks*